US006770286B1

(12) United States Patent
Berry (10) Patent No.: US 6,770,286 B1
(45) Date of Patent: Aug. 3, 2004

(54) PATCH APPLIQUES FOR TREATING DRY SKIN AND METHOD FOR THE PRODUCTION THEREOF

(75) Inventor: Craig J. Berry, Westport, CT (US)

(73) Assignee: SP Acupal Packaging, Inc., Mahwah, NJ (US)

( * ) Notice: Subject to any disclaimer, the term of this patent is extended or adjusted under 35 U.S.C. 154(b) by 441 days.

(21) Appl. No.: 09/613,186

(22) Filed: Jul. 10, 2000

(51) Int. Cl.⁷ .......................... A01N 25/34; A61K 9/00
(52) U.S. Cl. ....................................... 424/402; 424/400
(58) Field of Search ................................. 424/400, 402

(56) References Cited

U.S. PATENT DOCUMENTS 5,088,484 A * 2/1992 Freeman et al. ............... 602/44
6,063,398 A * 5/2000 Gueret ........................ 424/443

* cited by examiner

Primary Examiner—Thurman K. Page
Assistant Examiner—Humera N. Sheikh
(74) Attorney, Agent, or Firm—Perman & Green, LLP (57) ABSTRACT

A therapeutic skin patch for treatment of dry skin, includes a porous sheet-like body of inactive material, certain pores of said body being impregnated with solidified polyvinyl alcohol which contains a first combination of skin nutrients, and polyvinyl alcohol which occupies the pores of another portion of the body containing a second combination of skin nutrients, which second combination of skin nutrients is different from the first combination of skin nutrients. The polyvinyl alcohol which is contained in the pores of the one portion of the sheet-like body is characterized by a first color, and the polyvinyl alcohol which is contained in the pores of the other portion of the body is characterized by a second color that is different from the first color. The arrangement is such that the user can visually distinguish between the two portions and the corresponding skin nutrients contained in each, for the purpose of positioning the patch such that the colored sheet-like body can be applied with a predetermined desired orientation when the patch is initially applied to the skin.

41 Claims, 5 Drawing Sheets

PATCH APPLIQUES FOR TREATING DRY SKIN AND METHOD FOR THE PRODUCTION THEREOF

STATEMENT AS TO RIGHTS TO INVENTIONS MADE UNDER FEDERALLY-SPONSORED RESEARCH AND DEVELOPMENT

Research and development of the present invention and application have not been Federally-sponsored, and no rights are given under any Federal program.

BACKGROUND OF THE INVENTION

1. Field of the Invention

This invention relates generally to products for the treatment of dry skin, particularly dry skin on the face. It also relates to a method for using such products, and a method for the manufacture thereof.

2. Description of the Related Art Including Information Disclosed Under 37 CFR Sections 1.97–1.99

More particularly, the invention relates to variations in the method and apparati disclosed in applicant's U.S. Pat. No. 5,869,072, granted Feb. 9, 1999, and entitled METHOD FOR THE PRODUCTION OF A GLOVE, said application having common ownership with the present application.

The entire disclosure of U.S. Pat. No. 5,869,072 is specifically incorporated, by reference, into the present application in accordance with Section 608.01(p) of the Manual of Patent Examining Procedure.

Returning now to the issue that is addressed by the present invention, it is well known today that dry skin has been and continues to be a problem, not only for individuals in the teen-age group, but also for the public in general. With advancing age, a person experiences pronounced inability to maintain the condition of the skin, especially skin around the face, and more specifically the eyes. Wrinkles at the far corner of each eye, and dark circles under the eyes are well known phenomena, and efforts to cover up such undesirable characteristics constitute an ongoing field of research.

The problem can be stated simply as a person's natural inclination to be as attractive as possible, this going hand-in-hand with attempts to make the person look younger. Unfortunately, the emphasis on youth has become all-encompassing, as is well documented by the number of people who seek hair transplant and/or face lifts, particularly for those over 35 years of age.

As a consequence, there is a multitude of skin care products on the market, including various types of creams, lotions and oils.

In the decades subsequent to 1940, lotions incorporating homogenized oil-water mixtures were developed, the theory being that the water was, at least in part, absorbable into the skin, with the oil remaining on the skin so as to form a barrier. It was considered that the barrier restricted the inevitable evaporation which occurred, but in practice, evaporation was found to be an ongoing process, and the results obtained were marginal at best. Also, oil-based moisturizers suffer from the disadvantage of imparting to the skin a residual, greasy feel and appearance.

Subsequent discoveries included lotions containing urea, which is hygroscopic, and which has the ability to absorb and hold water in place on the skin itself. An undesirable side effect included inadvertent irritation to the skin, due to the fact that urea was somewhat on the base side, pH wise, and was capable of forming salts only when combined with a relatively strong acid.

Other ventures involved the use of lecithin, a naturally occurring substance derived from the soybean. It is generally considered to be a phospholipid, and is capable of absorbing relatively large amounts of water. A preparation containing this is purportedly sold under the trademark COMPLEX 15, manufactured by Key Pharmaceuticals.

Still other compounds involved the use of emulsions containing water, glycerine, mineral oil, alcohol, propylene glycol, lanolin, and fatty acids. Additional products comprise preparations known to contain what is known as Retin-A, a vitamin A derivative.

A-hydroxy-acids have also been used for skin treatment. While this class of product is often referred to as a moisturizer, in fact, the action of the A-hydroxy-acid is actually one involving a mild attack on the skin, wherein the outermost cells, which are likely to be the dry ones, are chemically extricated, and the remaining cells, previously lying below the outer layer, then become the new, outer layer. Naturally, these new cells, being younger and more protected, yield the desired result, namely a "new" skin look and feel, as well as increased moisture content, at least for the period immediately following the use of the A-hydroxy-acid.

Other methods of treatment involved what are known as "peeling agents", such as benzoyl peroxide; astringents, which firm up the tissues of the skin; and in some cases, oral or topical antibiotics, where infection is suspected to be a problem.

U.S. Pat. Nos. 4,591,501 and 5,302,377 are directed to related objectives in the treatment of dry skin.

In particular, Pat. No. 4,591,501 relates to a film that is produced by applying to a suitable base paper or material, a polypeptide, a plasticizer, and a polymer. The film, when moistened, will release the polypeptide and enable it to cover the skin. The nature of the polypeptide utilized is given in col. 1, line 61, namely, "'Polypeptide' as used herein, means and refers to polyamino acids derived from protein along with the proteins themselves. The polyamino acids useful in the practice of the invention are those . . . having a molecular weight of at least 3000. Preferably, the polyamino acids are derived from collagen."

Specific reference is made to the prior art cited during the prosecution of the application which matured into U.S. Pat. No. 4,591,501.

U.S. Pat. No. 5,302,377 relates to lotions for use as cold creams, after shaves, antiperspirants, skin moisturizers, and related functions. More particularly the patent involves a topical preparation prepared from a fatty alkoxylate ester. The patentee claims that such use of the preparation as an emollient, to smooth and soften skin, is superior to some prior known techniques, in that there is little or no oily or greasy feel experienced by the user, and thus the product is aesthetically more acceptable.

Finally, most of the creams and lotions on the market today utilize, of necessity, a preservative of some type, which can be irritating to the skin of the user. In essence, a preservative is a chemical that kills or controls bacteria, and application of such a compound to the skin, while deemed acceptable in limited amounts, is considered a potential hazard over the long term. An example of a preservative widely used is methylparaben, which is a crystalline compound $HOC_6H_4$—$COOCH_3$; it is the methyl ester of parahydroxybenzoic acid. Also, propylparaben is frequently used as a preservative. It is a crystalline ester, $HOC_6H_4COOC_3H_7$; it is sometimes referred to as propyl para-hydroxy-benzoate.

At least three "moisturizers" currently being marketed in this country, are known to contain propylparaben.

Failure to include a preservative in sufficient quantity to control bacterial growth can have serious consequences, as can well be appreciated when it is considered that skin care products are used by persons from infancy through the geriatric stage. This latter group is most susceptible to adverse side effects, and it is considered that wherever possible, use of preservatives in products which are ingested or topically applied, should be minimized to the greatest possible extent, since the potential hazardous long-term effects of chemicals in our environment is only recently, within the last decade or so, being considered to any great degree.

Finally, with most lotion/cream products, it is necessary to apply the substance and leave it on all day. This leads to inadvertent soiling of papers that may be handled as during office work. Products applied at bed time tend to be rubbed off onto the linens, as the user continuously and unconsciously, shifts position during sleep.

Accordingly there has existed a long-felt need for a product which can be applied to the skin for a relatively short time interval and without leaving a greasy look or feel to the skin, and thereafter perform its intended function and be discarded.

SUMMARY OF THE INVENTION

One object of the present invention is to provide a novel and improved beneficial skin applique which is extremely simple in its structure, and which is both effective in obtaining improved results and convenient to use.

Still another object of the invention is to provide an improved skin applique as above outlined, which contains ingredients that are substantially completely natural.

A related object of the invention is to provide an improved applique of the kind indicated, which does not utilize preservatives of any kind.

Still another object of the invention is to provide an improved applique in accordance with the foregoing, which is essentially completely chemically inactive during storage and shipping, and which becomes activated solely just prior to the use of the product by the consumer.

A further object of the invention is to provide an improved applique as above characterized, which has an extended shelf life, due to the inherently inactive nature of the product.

Still another object of the invention is to provide an improved applique as noted above, which can be inexpensively packaged in a watertight pouch, and sold in multiple units containing a plurality of individual pouches, each being wholly self-contained and totally inactive until just prior to use by the consumer.

The above objects are accomplished by a therapeutic applique for treatment of dry skin, comprising in combination a porous, flexible base member which is to be applied to the skin, and a water-activatable substantially solidified material carried on the surfaces of the member and permeating the pores thereof, the water-activated material having a moisture content of substantially less than 10% by weight, of the member, and wherein the material is soluble in water, so as to partially disassociate from the member and leach onto the skin of the user when water is applied to the exterior of the member while the latter is being worn.

The objects are further accomplished by a method of manufacturing a therapeutic member for treatment of dry skin, comprising the steps of mixing a quantity of water with polyvinyl alcohol, and heating the mixture so as to dissolve the alcohol in the water, applying the mixture onto a sheet, heating the sheet so as to reduce the water content to substantially less than 10% by weight of the sheet, and converting the polyvinyl alcohol substantially to a solid, cutting the sheet so as to form members of desired shapes, and sealing the members in substantially water-impervious containers, so as to shield them against moisture loss and thereby keep the solid polyvinyl alcohol in a water-inactive state until the consumer opens the package.

BRIEF DESCRIPTION OF THE DRAWINGS

In the drawings, illustrating a preferred embodiment of the invention.

DESCRIPTION OF THE PREFERRED EMBODIMENT

List of Reference Characters

8. Applique or patch
9. Mirror-image applique or patch
10. Vat or tub
12. Paddle
14. Heater
16. Storage tank
18. Storage tank
20. Outlet hose
22. Outlet hose
24. Pump
26. Pump
28. Hose
30. Hose
32. Doctor blade
34. Divider strip
36. Sheet of paper 37. Paper roll
38. Application station
40. Application station
42. Application station
44. Application station
46. Application station
48. Application station
52. Mesh or scrim
54. Pressure roller
56. Pressure roller
58. Composite sheet
62. Pull through roller
63. Pull through roller
64. Die roller
66. Bin
68. Water-tight packet
69. Scrap
70. Roll of scrap
72. Motor
74. Mesh portion
75. Applique or patch
76. Roll of composite
76'. Roll of composite storage
78. Paper portion
80. Idler roller
82. Oven
84. Nozzles
85. Pipe
86. Pump
88. Supply tank
90. Back-up roller
92. Mesh
94. Idler roller
96. Heated pressure roller
98. Heated pressure roller
103. Composite sheet
104. Composite sheet
105. Pull through roller
106. Pull through roller The present invention involves essentially the production and use of appliques or skin patches that are intended to be applied to the skin of a person, such appliques preferably taking the form of simple single-layer patches which can be oval or generally kidney-shape, or other outline. Each patch is intended to be placed in a desired position on the skin of the face, which preferably has been wetted with water just prior to application such that the patch will adhere to the skin, with an action to be described below.

Two quantities of water-based solution are produced, in accordance with the present invention. In a preferred example, one quantity is prepared and contains a yellow dye in an amount of typically less than ½ of one percent by weight, and the other solution contains a similar quantity of a blue dye. However, other color arrangements or combinations could be used as well, and the present invention is not intended to be limited to solely the yellow and blue dyes noted.

Figures 1, 2:
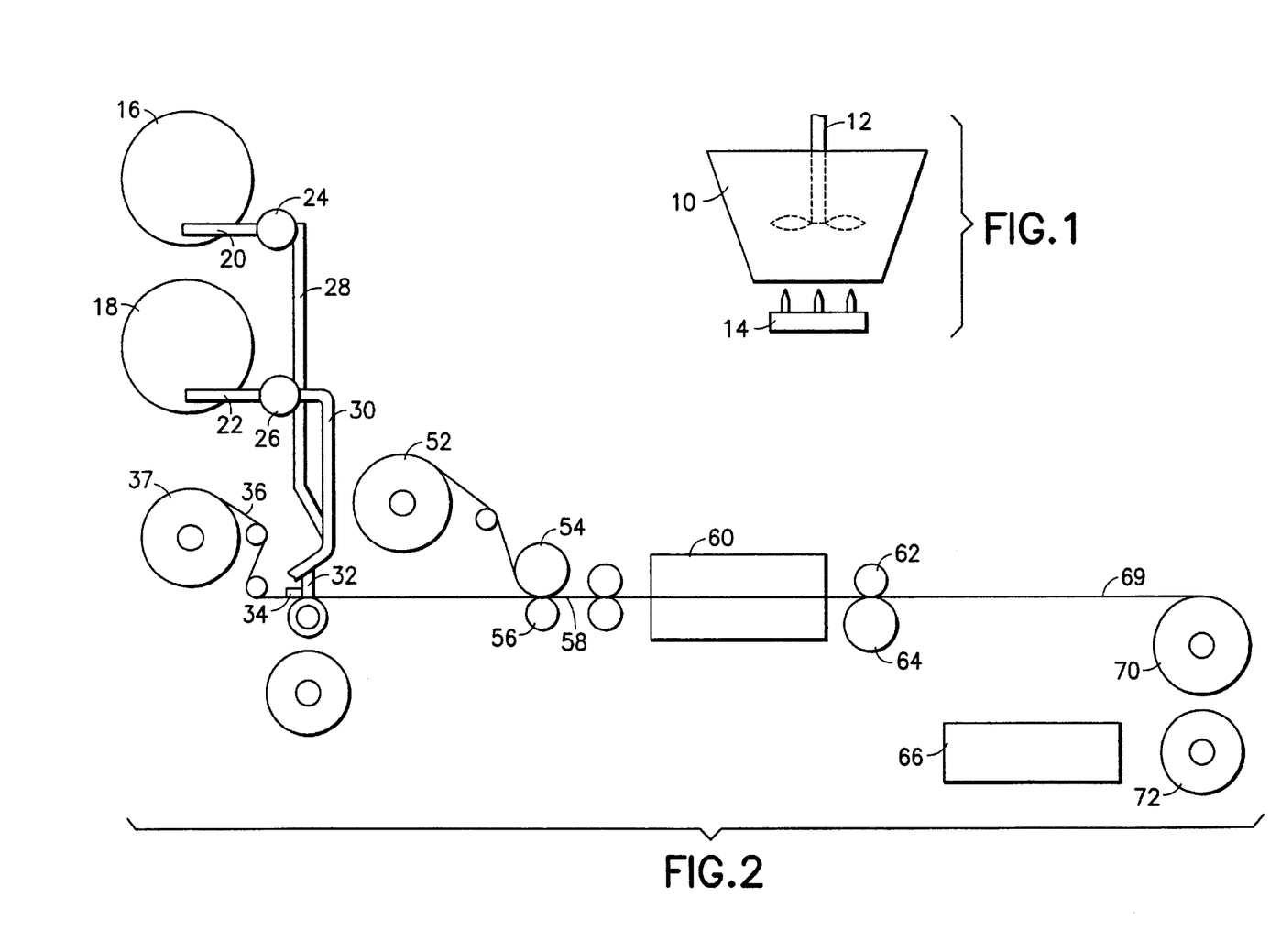
FIG. 1 is a diagrammatic side elevational view of a heated vat or tub as used for mixing ingredients.
FIG. 2 is a diagrammatic representation of an apparatus showing the various steps utilized in carrying out the invention.

In preparing the first solution containing a yellow dye, FD&C yellow is preferably used. A vat or tub generally designated 10 is filled with a quantity of pure, cold water. Pellets of polyvinyl alcohol, which may be of a type sold under the Trademark AIR VOL 523, are introduced into the cold water in the vat, along with the yellow dye. The pellets are small in size, sufficiently so to be characterized as granular in nature. As the pellets are being introduced into the vat, a paddle 12 is activated to stir the water, and in addition, the vat is heated up to a temperature on the order of 140–165 degrees F. by a heater 14, for a period of up to 3–4 hours, depending on the time required for the polyvinyl alcohol pellets to completely dissolve in the hot water.

The solution is admixed with extracts of vitamins A, C and E, together with other, optional nutrients which include, but are not limited to substances that sooth, heal, and/or moisturize the skin.

For example, other optional ingredients comprise PG-865 propylene glycol; Phospholipid EFA, a moisturizer comprising Linoleamidopropyl PG-Dimonium Chloride Phosphate; AMG-O, comprising Oleamidopropyl PG-Dimonium Chloride, a surfactant; Honey, AJIDEW N-50, comprising sodium PCA, moisture retention salt; VEGEPLEX 2500, which is a botannical extract complex; and Aloe Vera, which moisturizes, soothes and heals.

Additionally, there may be included Extracts of the following: Cranesbill, Comfrey, Elder Flower, Calendula, Tormentil, Plantain, Horsetail, Burdock, and Cucumber. In some of the appended claims the polyvinyl alcohol is considered to be a water-activatable substance, since the polyvinyl alcohol is solid when dry, but dissolves readily in water.

In a preferred embodiment, the yellow solution contains a combination of elements, some or all of which are taken from the ingredient list in the previous two paragraphs. In a similar manner, the blue solution contains a combination which preferably contains some or all of the elements of the yellow solution, but in addition, contains vitamin K, kojic acid derivative. The yellow solution is devoid of the vitamin K.

During the production of the patches of the invention, there are provided two storage tanks 16 and 18, one containing a solution having the yellow dye, and the other containing a solution having the blue dye. Each tank has an outlet hose 20, 22, and each hose connects with a pump 24, 26, respectively. The outlet of each pump is connected to hoses 28 and 30 respectively that extend downwardly to a doctor blade 32, sometimes known as a knife-over-roller device.

Figure 3:
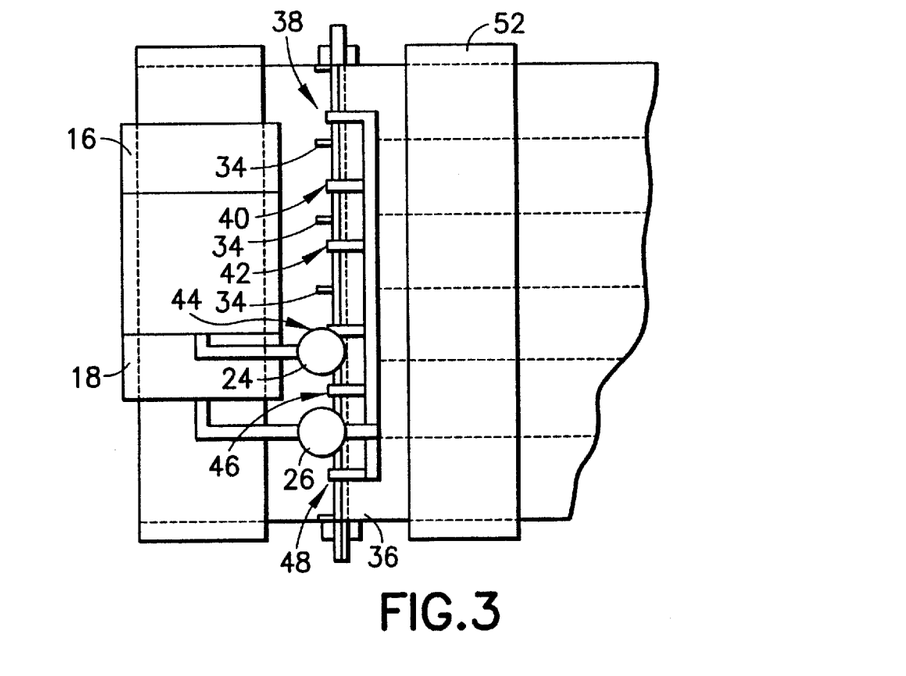
FIG. 3 is a fragmentary top plan view of the apparatus of FIG. 2.
Figure 4:
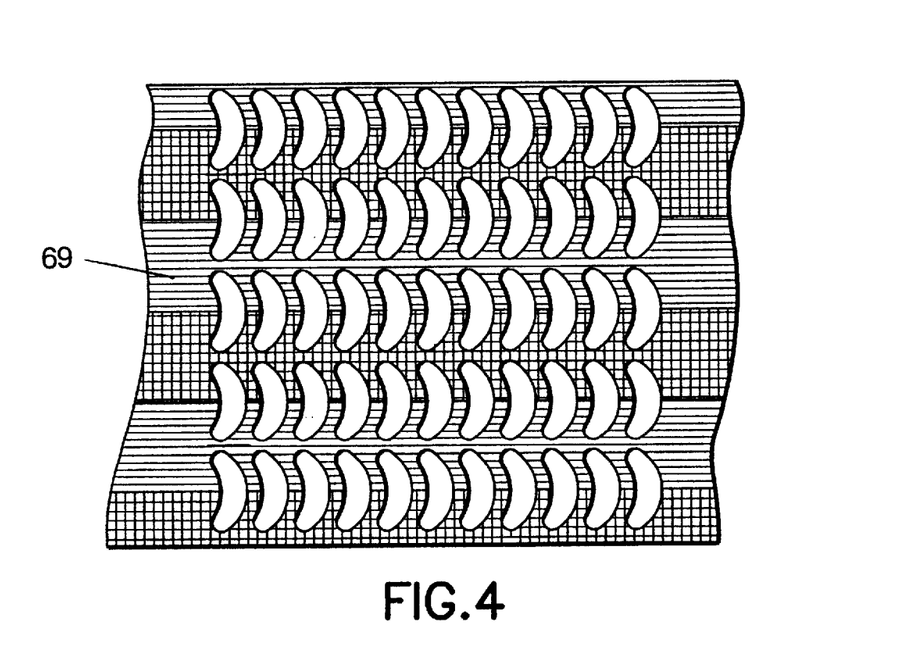
FIG. 4 is a top plan view of a portion of the composite scrap sheet as it comes from the apparatus of FIGS. 2 and 3.

In accordance with the invention and referring to FIG. 3, there is disposed on the upstream side of the doctor blade 32 a series of plastic divider strips 34, which in practice are about 1 inch high, and 3 inches long. A total of 5 divider strips is utilized, and a sheet of wax- or silicon-backed paper 36 from a roll 37 passes under the strips 34 prior to contacting the doctor blade 32. With the arrangement shown, a total of 6 application stations 38, 40, 42, 44, 46 and 48 is used, being fed by the tubing 28, 30 from the output of the respective pumps. At a first station 38, the open end of a tube drips the solution having the blue color onto the paper 36 from the roll 37. One of the divider strips 34 confines the blue solution, which is somewhat more viscous than water, to the edge area of the paper 36.

A similar tube feeds station 40, except the tube is from the tank 18 having the yellow mixture, and the open end of a tube drips onto the paper 36 at this station 40.

Similarly, additional hoses 28, 30 respectively feed stations 42, 44, 46 and 48. The result is that the paper 36 emerges from the doctor blade 32 with alternating strips of yellow and blue slurry or slush thereon, still in a wet condition, and wherein the slush has a thickness of 2.5 mils, typically.

Subsequently, from a supply roll of nylon or plastic mesh, or scrim 52 comprising a porous sheet-like body of inactive material, there is a continuous feed over and onto the paper 36 as the paper moves. A pair of pressure rollers 54, 56 is provided downstream of the doctor blade 32, and the superposed mesh and paper are forced against one another, with the still-wet slurry therebetween. The arrangement is such that a two-layer assemblage or composite sheet 58 is produced, one layer consisting of the paper 36, and the second layer consisting of the scrim 52. The slurry comprising various colored stripes of polyvinyl alcohol and water remain intact as the mesh and wax paper pass through the rollers 54, 56. The pores of the mesh are filled with the slurry of polyvinyl alcohol and water.

Immediately following the pressure rollers 54, 56 the composite sheet 58 enters a series of ovens or furnaces 60, which remove all but 6 to 8percent of the water that is present. The polyvinyl alcohol and water mixtures thus dry to the extent that they become somewhat adhesive and thereby bind the scrim 52 to the paper 36 after the composite sheet 58 exits the furnaces.

Subsequently the composite sheet 58 passes between cooperable die rollers 62, 64 which punch out the oval or kidney-shaped patches 8, FIG. 6, from the composite sheet 58. Some of the patches fall from the sheet 58 by gravity, while others are manually removed by workmen who stand at the die rollers 62, 64 and knock out any remaining patches that have inadvertently clung to the composite sheet 58.

Figure 10:
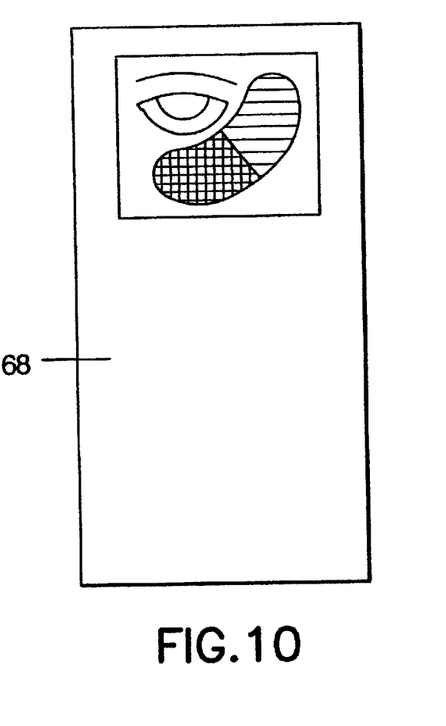
FIG. 10 is a plan view of a water-tight package for the skin patches of the present invention.

The patches 8 are collected in a bin 66, for subsequent packaging in water-tight packets 68. What remains of the composite sheet is collected as scrap 69 on a scrap roll 70 powered by a motor 72, and is discarded.

The nature of the packaging for the patches is an important factor in the production of a patch of the invention. Since the patches are provided sealed in the moisture-resistant pouch 68, there exists insufficient water for the formation of bacteria. In a preferred embodiment, the pouch 68 consists of a 3½ mil. metallic foil laminated onto a polyethylene film.

In this connection, it is noted that many prior art skin treatment products are water based. Where water-based materials are utilized, it is usually necessary to include an anti-bacterial agent, which in effect is a mild poison.

In contrast, by the present invention no preservatives are required. Accordingly, there is no chance of irritation to the skin of the user, because all of the ingredients are natural, and no anti-bacterial chemicals are needed. Stated differently, the patch is inactive as long as it remains dry. Adding water to the dry patch renders it active at the time the consumer opens the foil and lays the patch on his skin, and/or adds water to it. Thus the product of the invention is very beneficial for people who have sensitive skin, and/or who are allergic to preservatives. Generally, the fewer ingredients which might be irritating, the better.

In accordance with the invention, the die rollers 62, 64 are positioned with respect to the incoming composite sheet 58 in such a way that each patch 8 is cut so that one portion of the patch is derived from the yellow area that contains a particular combination of skin nutrients thereon, and another portion of the same patch is derived from the blue area, which contains a combination of skin nutrients that is different from the first combination. As a consequence, where the combinations of skin nutrients of the yellow and blue areas differ, a double-function skin patch is realized.

Figure 6:
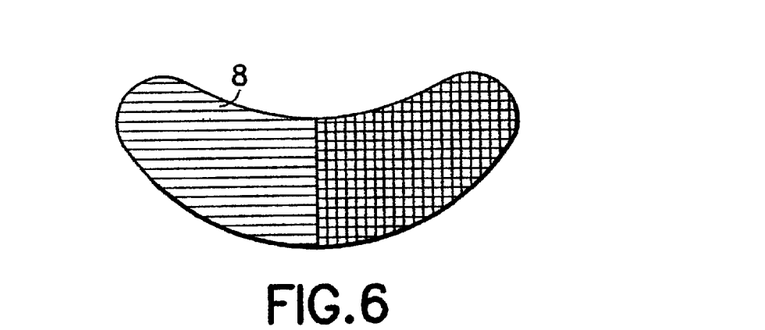
FIG. 6 is a plan view of one skin patch as made with the apparatus of FIG. 2.
Figure 7:
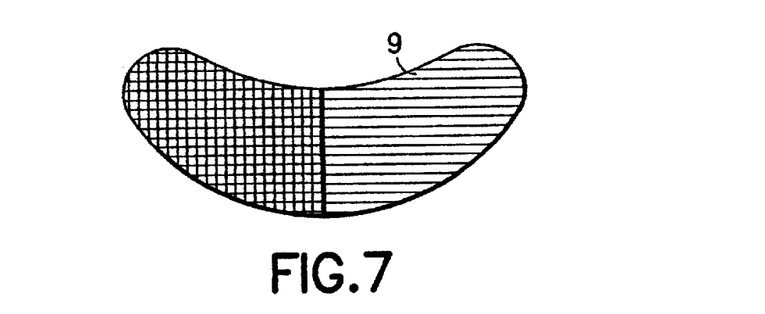
FIG. 7 is a plan view of a similar skin patch but constituted as a mirror image of the patch of FIG. 6.

In the case of crescent-shaped patches of the type shown in FIGS. 6 and 7 it is noted that these are symmetrical pairs, for application to the left and right eye simultaneously and with a predetermined orientation. That is, the patch 9 of FIG. 7 is the mirror image of the patch 8 shown in FIG. 6.

Figure 11:
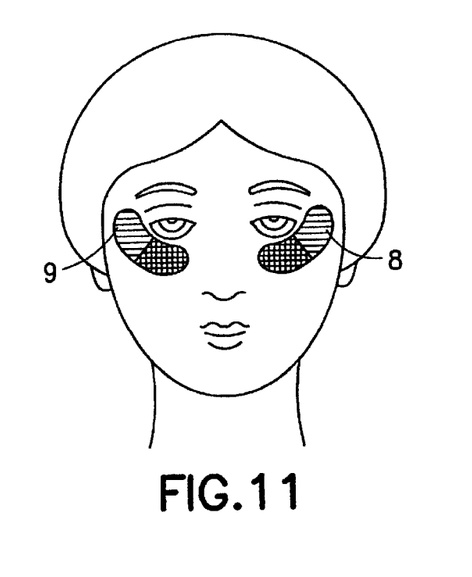
FIG. 11 is a diagrammatic representation of a person's face, and showing water-activatable appliques in the form of kidney-shaped patches in position around the person's eyes.

In a preferred embodiment, the skin nutrient characterized by the yellow color contains polyvinyl alcohol and some or all of the substances noted above, typically vitamins A, C and E, whereas the skin nutrient characterized by the blue color contains, in addition, vitamin K, or Kojic acid derivative. The kojic acid has the ability to lighten the skin, and accordingly when the user is applying the patches to his face, he is instructed to position the blue portion below the eyes, where dark circles tend to form as a natural part of the aging process. The yellow portion of the patch is positioned to the outer side of the eye socket near the edge of the eyebrow, and contains some or all of the skin nutrients as above described, but which omits the vitamin K, since this is not needed here. The addition of Kojic acid might produce an undesirable lightening to this outer area of the face, which would be aesthetically undesirable. Correct positioning of two patches of the invention is shown in FIG. 11, wherein the blue end of the patch, containing the Kojic acid, is positioned under the eye.

The patches, when removed from their water-impervious packaging are inactive. The addition of water to the patch prior to application dissolves some of the polyvinyl alcohol, and renders the patch active prior to contact with the skin.

As an alternative, the user can first wet the skin, and then immediately apply the dry patches to the wet skin. Under this circumstance, the inside surface of the patch becomes tacky and sticks the entire patch to the skin. The outside surface of the patch may begin to dry by evaporation, which is desirable since the drying polyvinyl alcohol and water mixture tend to captivate the moisture on the skin below, by forming an occlusive layer of dried polyvinyl alcohol, or partially dried polyvinyl alcohol. This layer prevents or diminishes evaporation of moisture below, which latter is in contact with the skin.

Any air bubbles which may inadvertently form between the skin and the patch can be readily smoothed out by the user. Also the position of a patch can be adjusted with the fingers, as needed. FIG. 11 shows a person's face with patches applied thereto.

The dies cut the patches or objects 8, 9, and they emerge from the die-cut machine. There is a certain amount of waste from the procedure. Such waste is discarded, not recycled.

Figure 8:
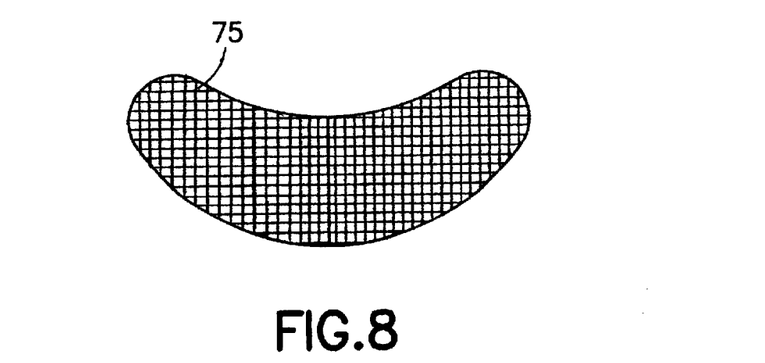
FIG. 8 is a plan view of a skin patch having pressure-sensitive adhesive protected by a release paper backing.
Figure 9:
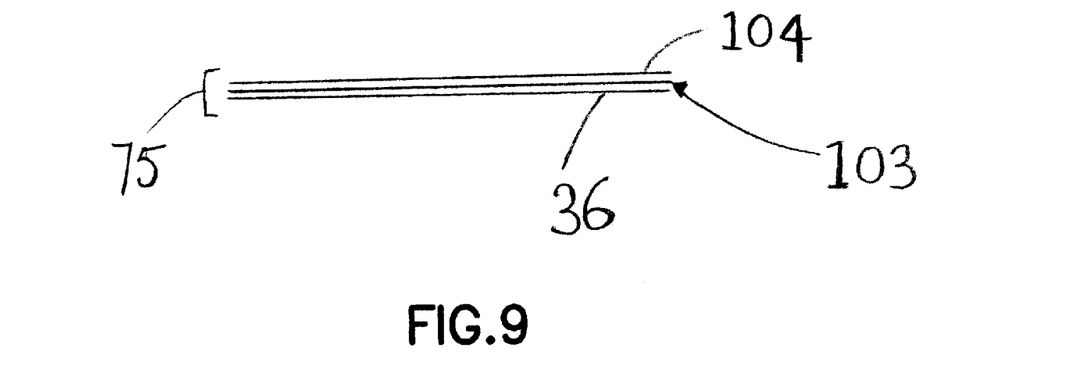
FIG. 9 is a plan view of a patch similar to that of FIG. 8 but constituted as a mirror image of the patch of FIG. 8.

Another embodiment of the invention is illustrated in FIGS. 8 and 9 wherein the patch 75 of FIG. 8 and the patch 75 of FIG. 9 are produced from at least two layers of the composite sheet, and as many as three. These are especially produced so that the top layer 104 of the composite sheets masks the color of the composite sheet beneath it 103 so that when the patch is activated by water, the color of the composite sheet 104 of FIG. 9 begins to mix with the color of composite sheet 103 of FIG. 9 and effect a color change in the top composite sheet 104 of FIG. 9. This is desirable because it indicates to the user that the patch is functioning. The thickness of the composite layers can also be predetermined so that the timing of the color change can be controlled and thereby used to effect a color change over a specific period of time which can be used to indicate to the user that the patch has completed it's function and can therefore be removed from the skin when a specific color has materialized.

Figure 5:
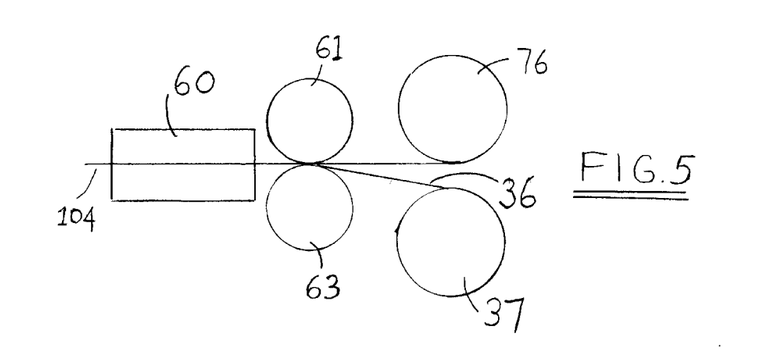
FIG. 5 is a diagrammatic representation of another embodiment of the invention wherein the skin patches have pressure-sensitive adhesive and do not require wetting.

As shown in FIG. 5, the furnace 60 which receives the composite sheet 104 as in the previous embodiment of the invention can be utilized. After the composite sheet 104 leaves the oven 60 and the pull-through rollers 61 and 63 it is separated into its components 104 and silicone-backed paper 36. The silicone-backed paper 36 can be rolled up for reuse. The composite sheet 104 is rolled up in the roll 76.

Figure 12:
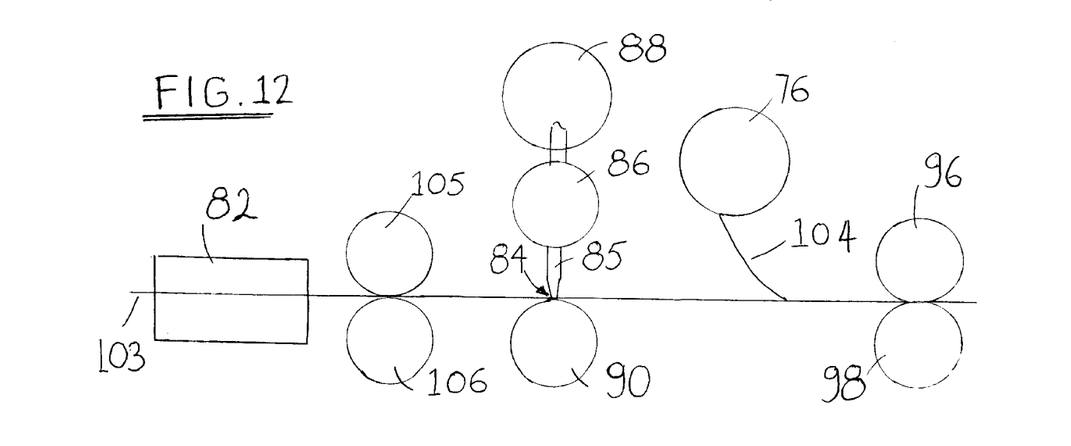
FIG. 12 is a diagrammatic representation of another embodiment of the invention wherein a composite sheet is produced.

As shown in FIG. 12, The composite sheet 103 is produced in a second oven 82. This composite sheet is produced without the addition of the nylon mesh as described in the previous embodiment of the invention.

In the area between the rollers 106 and 90, the composite sheet 103 is coated with water from nozzles 84 that are fed through a horizontal pipe 85 and pump 86 from a supply tank 88. The composite sheet 103 is backed up by a roller 90 at the coating point where the nozzles 84 are located, as shown.

After leaving the roller 90, the composite sheet 103 is overlaid by composite sheet 104 and finally brought through heated pressure rollers 96 and 98, which bonds the composite sheet 104 to the composite sheet 103. Thereafter the composite can be die cut as by the rollers 62 and 64 to produce various shapes.

It will now be seen that I have provided, by the present invention, improved therapeutic appliques or patches having unique properties by which the skin tone and appearance can be greatly enhanced when they are applied to the various areas of the human body. The patches are small and convenient to use, and effective for their intended purpose.

Variations and modifications are possible without departing from the spirit of the invention.

Each and every one of the appended claims defines an aspect of the invention which is separate and distinct from all others, and accordingly it is intended that each claim be treated in this manner when examined in the light of the prior art devices in any determination of novelty or validity.

What is claimed is:

1. A therapeutic skin patch for treatment of dry skin, comprising in combination:
   a) a porous sheet body of inactive material,
   b) the pores of said body being impregnated with solidified polyvinyl alcohol,
   c) the polyvinyl alcohol which occupies the pores of one portion of said body containing a first combination of skin nutrients, and the polyvinyl alcohol which occupies the pores of another portion of said body containing a second combination of skin nutrients, which second combination of skin nutrients is different from the first combination of skin nutrients,
   d) the polyvinyl alcohol which is contained in the pores of said one portion of the sheet body being characterized by a first color, and
   e) the polyvinyl alcohol which is contained in the pores of said other portion of the body being characterized by a second color that is different from the first color, whereby the user can visually distinguish between the said two portions and the corresponding skin nutrients contained in each, for the purpose of positioning the patch such that the colored sheet body can be applied with a predetermined desired orientation when the patch is initially applied to the skin.

2. A therapeutic skin patch for treatment of dry skin as set forth in claim 1, wherein the colors of the portions are respectively blue and yellow.

3. A therapeutic skin patch as set forth in claim 1, wherein one of said portions contains, in addition to the impregnated polyvinyl alcohol, vitamins A, C, and E.

4. A therapeutic skin patch as set forth in claim 3, wherein the other of said portions contains, in addition to the impregnated polyvinyl alcohol, vitamins A, C, E, or vitamin k-kojic acid derivative.

5. A therapeutic skin patch as set forth in claim 1, wherein the sheet body has a generally crescent shape, with one end of the crescent containing said one portion, and the opposite end of the crescent containing said other portion.

6. A therapeutic skin patch as set forth in claim 2, wherein the portion having the yellow dye contains the vitamin k-kojic acid, and is adapted for placement around the eye where dark circles tend to occur.

7. A therapeutic skin patch as set forth in claim 1, wherein the portion having the blue dye is devoid of the vitamin k-kojic acid, and is adapted for placement on the skin outside the respective eye.

8. A therapeutic skin patch as set forth in claim 1, wherein the polyvinyl alcohol and nutrients are inactive when the patch is in a dry condition, and become active upon contact with water during which time the applied patch releases the said vitamins and allows them to leach into the skin.

9. A therapeutic skin patch as set forth in claim 1, wherein said patches, when in a dry condition, contain moisture in an amount that is substantially less than 10% by weight, of the patch body.

10. A therapeutic skin patch as set forth in claim 1, wherein said patch, when applied to wet skin, allows the polyvinyl alcohol and dissolved skin nutrients to leach into the skin, and with time, the outside layer of said patch experiencing limited evaporation of water whereby the water on the inner surface of the patch is held captive against and in contact with the skin by the formation of an occlusive layer of dried polyvinyl alcohol on the outer surface of the body.

11. A therapeutic skin patch as set forth in claim 1, wherein said patch body is constituted of a material selected from the group consisting of scrim, nylon mesh, and plastic mesh.

12. A therapeutic skin patch for treatment of dry skin, comprising in combination:
   a) a porous sheet body of inactive material,
   b) the pores of said body being impregnated with a water-activatable substance,
   c) the water-activatable substance which occupies the pores of one portion of said body containing a first combination of skin nutrients, and the water-activatable substance that occupies the pores of another portion of said body containing a second combination of skin nutrients, which second combination of skin nutrients being different from the first combination of skin nutrients, and
   d) the water-inactivatable substance which occupies the pores of said one portion of the sheet body being dyed with a first color, and
   e) the water-activatable substance which occupies the pores of said other portion of the body being dyed with a second color that is different from the first, whereby the user can visually distinguish between the two portions and the corresponding skin nutrients contained in each, for positioning the patch such that the colored sheet body can be applied with a predetermined orientation when the patch is initially applied to the skin.

13. A therapeutic skin patch as set forth in claim 12, wherein said water-activatable material of said patch body comprises polyvinyl alcohol.

14. A therapeutic skin patch as set forth in claim 1, wherein the patch body is flexible when dry, and can readily be applied to the skin around the eye, by the fingers of the user, said patch body adhering to the skin by a partial dissolution of the polyvinyl alcohol, which dissolution adds tackiness to the patch.

15. A therapeutic skin patch as set forth in claim 1, wherein the patch can be positioned and re-positioned by the fingers after initial application to the skin.

16. A therapeutic skin patch as set forth in claim 1, wherein air bubbles tend to form between the patch and the skin when the latter is wetted, said air bubbles being capable of being smoothed out with the fingers.

17. A therapeutic skin patch as set forth in claim 1, wherein the patch body is formed by die-cutting, to a crescent shape.

18. A therapeutic skin patch as set forth in claim 1, and further including a wax paper backing, constituting a peel-off sheet which is removed from the patch body just prior to use of the patch.

19. In a work station having a doctor blade, a roller and a series of divider strips disposed on one side of the doctor blade, the method of manufacturing a therapeutic patch for treatment of dry skin, comprising the steps of:
   a) mixing a quantity of water with polyvinyl alcohol, and heating the mixture so as to dissolve the polyvinyl alcohol in the water,
   b) separating the mixture into two portions, thereafter adding to one portion a dye having a first color, and adding to the other portion a dye having a second color which is different from the first color,
   c) drawing a length of elongate, wax or silicon-coated backing paper from a supply roll, past said work station and just beneath said divider strips and doctor blade,
   d) transferring the mixture containing the first color to the doctor blade and depositing the mixture between two adjacent divider strips,
   e) transferring the mixture containing the second color to the doctor blade and depositing the mixture between the one of said two adjacent divider strips and a third one of said divider strips, so as to produce on the upper surface of the wax or silicon-coated backing paper, two coextensive strips of liquid of different color after the wax or silicon-coated backing paper passes beneath the doctor blade,
   f) applying to the wetted wax or silicon-coated paper, a length of porous carrier material so as to form two superposed sheets, one of wax or silicon-coated paper and the second of the porous carrier material, with the wetted mixtures of water and polyvinyl sandwiched therebetween,
   g) heating the superposed sheets so as to reduce the water content of the superposed layers, and to convert the polyvinyl alcohol substantially to a solid condition,
   h) die-cutting the dried superposed layers so as to form a patch having at one end, solidified polyvinyl alcohol of said first color, and having at its other end, solidified polyvinyl alcohol of the second color, so as to produce a dual-color patch, and
   i) sealing the patch in a substantially water-impervious container, so as to shield the patch against moisture and thereby keep the solid polyvinyl alcohol in a water-inactive state until the consumer opens the package.

20. The method of manufacturing a therapeutic skin patch as set forth in claim 19, wherein the polyvinyl alcohol is added to the water in granular form, and the resulting mixture is heated to a temperature of up to 165 degrees F.

21. The method of manufacturing a therapeutic skin patch as set forth in claim 19, wherein the mixture of polyvinyl alcohol and water is heated and mixed for a period of from 3 to 4 hours.

22. The method of manufacturing a therapeutic skin patch as set forth in claim 19, wherein following the step of depositing the mixtures, the further step of applying the porous carrier material with sufficient pressure to cause the mixture to impregnate the pores of the porous carrier material, and thereafter, drying the superposed wax paper and porous carrier material and polyvinyl alcohol-water mixtures contained therebetween.

23. The method of claim 19, wherein the therapeutic patch is substantially devoid of preservative chemicals.

24. The method of claim 19, wherein the thickness of the mixture after the wax or silicon-coated paper has passed the doctor blade is on the order of several thousandths of an inch.

25. A method of imparting moisture to the skin of a person, comprising the steps of:
   a) forming a patch of porous material, and impregnating one portion of the patch with a quantity of polyvinyl alcohol containing a combination of skin nutrients and containing a colored dye,
   b) impregnating another portion of the patch with a quantity of polyvinyl alcohol containing a combination of skin nutrients which is different from the first combination of skin nutrients, and containing a dye which is of a color that is different from the color of said first dye,
   c) heating the patch and impregnated polyvinyl alcohol so as to reduce the water content of the patch to an extent sufficient to solidify the polyvinyl alcohol on the surfaces and in the pores of the patch,
   d) applying the patch to the skin with a predetermined color orientation, so as to position the portion of the patch having the first combination of skin nutrients over one part of the skin, and to position the portion of the patch having the second combination of skin nutrients over another part of the skin, and
   e) applying water to the exterior surface of the patch so as to partially dissolve the polyvinyl alcohol and allow it to directly contact and saturate the skin, for an extended length of time.

26. The method as set forth in claim 25, wherein:
   a) the polyvinyl alcohol at the outer surface of the patch is allowed to air dry, so as to form an occlusive barrier layer which minimizes evaporation of water from the polyvinyl alcohol that is in direct contact with the skin, between the latter and the porous material of which the glove is constituted.

27. The method as set forth in claim 25, wherein:
   a) the skin is first wetted with water, prior to application of the patch to the skin.

28. A therapeutic skin patch for treatment of dry skin as set forth in claim 1, consisting of at least two separate layers, of different colors, which change color when activated by water to inform the user that the product is actively performing its desired function.

29. The therapeutic skin patch of claim 1 wherein the skin patch is substantially free of preservative chemicals.

30. The therapeutic skin patch of claim 1 wherein the skin patch is a double function skin patch, wherein when the body is applied to the skin, the first combination of skin nutrients in the one portion is adapted to function on a first section of the skin under the body and the second combination of skin nutrients on another portion is adapted to function on a second section of skin under the body.

31. The therapeutic skin patch of claim 1 wherein the solidified polyvinyl alcohol forms a connected layer of film having a minimal residual moisture content.

32. The therapeutic skin patch of claim 12 wherein the material is adapted to partially disassociate from the body and leach onto the skin of the user when water is applied to an exterior surface of the body while the skin patch is applied to the skin.

33. The therapeutic skin patch of claim 12 wherein the material forms a connected layer of a film having a residual moisture content of substantially less than 10% by weight of the film layer.

34. The therapeutic skin patch of claim 12 further comprising a layer adapted to change color when activated by water to inform the user that the patch is functioning.

35. The therapeutic skin patch of claim 34 wherein a thickness of the layer is varied to control the color change.

36. The therapeutic skin patch of claim 1, wherein the patch is adapted to be stored in a substantially dry state and wetted when the patch is applied to the skin in order to activate the first combination and the second combination.

37. The therapeutic skin patch of claim 1 wherein the nutrients include substances that sooth, heal or moisturize the skin.

38. The therapeutic skin patch of claim 1 wherein the patch does not include anti-bacterial chemicals.

39. The therapeutic skin patch of claim 1 wherein the patch is stored in a dry state and remains inactive in the dry state.

40. The therapeutic skin patch of claim 39 wherein adding water to the dry patch activates the patch.

41. The therapeutic skin patch of claim 39, wherein the stored patch, in the dry state, has a moisture content that is less than 10% by weight of the patch body.

* * * * *